United States Patent [19]

Friese et al.

[11] Patent Number: 5,435,901
[45] Date of Patent: Jul. 25, 1995

[54] ELECTROCHEMICAL MEASURING SENSOR

[75] Inventors: Karl-Hermann Friese, Leonberg; Helmut Weyl, Schwieberdingen; Werner Wieland, Kornwestheim, all of Germany

[73] Assignee: Robert Bosch GmbH, Stuttgart, Germany

[21] Appl. No.: 121,961

[22] Filed: Sep. 15, 1993

Related U.S. Application Data

[63] Continuation of Ser. No. 781,191, filed as PCT/DE90/00539, Jul. 18, 1990, abandoned.

[30] Foreign Application Priority Data

Aug. 18, 1989 [DE] Germany ............... 39 27 283.4

[51] Int. Cl.⁶ .......................................... G01N 27/409
[52] U.S. Cl. ................................ 204/429; 204/424; 204/427
[58] Field of Search ............... 204/153.18, 421–429

[56] References Cited

U.S. PATENT DOCUMENTS

| | | | |
|---|---|---|---|
| 3,597,345 | 8/1971 | Hickam et al. | 204/427 |
| 3,598,711 | 8/1971 | Flais | 204/427 |
| 3,645,875 | 2/1972 | Record | 204/429 |
| 3,978,006 | 8/1976 | Topp et al. | 204/429 |
| 4,119,512 | 10/1978 | Inoue et al. | 204/429 |
| 4,121,988 | 10/1978 | Sano et al. | 204/429 |
| 4,174,258 | 11/1979 | Bode | 204/429 |
| 4,292,158 | 9/1981 | Muller et al. | 204/426 |
| 4,334,940 | 6/1982 | Habdas et al. | 204/426 |
| 4,347,113 | 8/1982 | Fischer et al. | 204/428 |
| 4,356,065 | 10/1982 | Dietz | 204/429 |
| 4,379,741 | 4/1983 | Sano et al. | 204/429 |
| 4,383,906 | 5/1983 | Sano et al. | 204/429 |
| 4,452,687 | 6/1984 | Torisu et al. | 204/428 |
| 4,507,191 | 3/1985 | Ebizawa et al. | 204/427 |
| 4,626,337 | 12/1986 | Hotta et al. | 204/427 |
| 4,786,399 | 11/1988 | Wertheimer et al. | 204/427 |

FOREIGN PATENT DOCUMENTS

2619748 11/1977 Germany.
3735298 5/1988 Germany.

OTHER PUBLICATIONS

Friese, Weyl, Wieland & Wiedenmann, Abstract of DE-OS 37 35 298, May 1988, corresponding to EP 393,038 of Oct. 24, '90. There is a corresponding U.S.S.N. 372,363.

R. Bosch GmbH, Abstract of DE-OS 26 19 746 of Nov. 24, '77.

*Primary Examiner*—T. Tung
*Attorney, Agent, or Firm*—Frishauf, Holtz, Goodman & Woodward

[57] ABSTRACT

An electrochemical measuring sensor is proposed for determining the oxygen content in exhaust gases which has a base body made of an ion-conducting solid electrolyte in the form of a tube closed at one end, an inner electrode, an outer electrode disposed on the external surface of the probe block and having a conductor track on the connection side which has a covering layer, a ceramic protective layer and a metallic sealing ring for sealing the reference space from the exhaust gas space and for making an electrical contact to the housing in which the measuring sensor is to be inserted. The electrochemical covering layer covering the conductor track is brought down on the reference side of the probe block to below the metallic sealing ring and the track is formed with uncovered lateral extensions making electrical contact with the ring. This makes it possible to significantly prolong the service life of the measuring sensor.

7 Claims, 1 Drawing Sheet

ELECTROCHEMICAL MEASURING SENSOR

This application is a Continuation of application Ser. No. 07/781,191, filed as PCT/DE90/00539, Jul. 18, 1990, now abandoned.

FIELD OF THE INVENTION

The invention relates to an electrochemical measuring sensor for determining the oxygen content in exhaust gases.

BACKGROUND

It is generally known to use electrochemical measuring sensors—often also referred to as λ-probes for determining the oxygen content in exhaust gases, in particular in exhaust gases of internal combustion engines.

Known measuring sensors of this type are based on the principle of the oxygen concentration cell incorporating an ion-conducting solid electrolyte and forming a base body of the sensor. They are composed, for example, of a tube, closed at one end, made of an ion-conducting solid electrolyte on whose external surface, facing the exhaust gas of a porous platinum layer is applied, forming one electrode, and which simultaneously catalyses the thermodynamic equilibrium as best as possible. Such an establishment of the gas equilibrium is necessary since the gas is generally not in thermodynamic equilibrium at the outset. Thermodynamic is a condition for as sharp a potential change as possible to occur at $\lambda=1$ or, when in the case of a polarographic diffusion current probe (cf. German Patent Specification 27 11 880) and corresponding U.S. Pat. No. 4,356,065, Diety/Bosch, the respective actual λ-value is to be determined.

In these measuring sensors, the electrode layer, for example a platinum layer, is very thin and although it generally carries a porous ceramic protective layer, it is nevertheless subject to corrosive attack after prolonged use by some of the exhaust gas constituents, for example soot, lead, phosphorous compounds and sulphur compounds. This corrosive attack takes place over the entire surface of the measuring sensor, but is particularly severe towards the open end, where, as a consequence of a lower temperature, these harmful constituents deposit more easily and do not volatilize again so readily, and where the electrode layer is under some circumstances no longer completely covered by the porous protective layer, which is only of limited effectiveness in any case.

German Auslegeschrift 26 19 746 discloses an electrochemical measuring sensor which has, on the external surface of the solid electrolyte base body or probe block facing the exhaust gas, an electron-conducting layer in the form of a conductor track made of a mixture of electron-conducting material, which catalyses the establishment of the gas equilibrium, and, optionally, ceramic material or glass as a supporting structure which extends from the closed end to the open end and in which the part of the conductor track facing the open end of the tube is covered with a glaze, for example, made of potassium aluminosilicate, barium aluminosilicate or barium calcium aluminosilicate.

It has been found, however, that the covering of the conductor track with glaze as described in German Auslegeschrift 26 19 746 has several serious disadvantages. A disadvantage of using such covering layers is, first of all, that said covering layers can be applied only after the sintering process. A disadvantage is, furthermore, that cracks which easily expose the conductor tracks to a local attack easily arise during the operation of the measuring sensors in the covering layers produced on the glazings because of their very different material composition from the probe ceramic and, consequently, their different thermal expansion.

In the measuring sensor disclosed by German Patent Specification 37 35 298 and corresponding U.S. Ser. No. 06/372,363, filed 1978, the disadvantages of the measuring sensor disclosed by German Auslegeschrift 26 19 746 are eliminated by producing the covering layer from the raw material mixture of the probe block ceramic with the same or enhanced sintering activity, for example from stabilized $ZrO_2$ to which a flux is optionally added.

It has, however, been found that, even in the case of these measuring sensors, in which the covering layers of the conductor tracks on the reference gas side of the probe block are not brought down to below the metallic sealing ring, the service life is still not completely satisfactory, in particular in hot applications or when operated with leaded gasoline.

THE INVENTION

The covering layer covering the conductor track on the reference gas side of the base body is brought to beneath the metallic sealing ring, and the track is formed with contacting regions contacting the sealing ring, extending laterally from the track. This has substantial advantages.

Surprisingly, it has been found that the service life of the measuring sensor of the type described can be very substantially prolonged by protecting the connection side of the outer conductor track against chemical and erosive attack in the contact region by bringing the covering layer to below the metallic sealing ring. It is only here that the actual conductor track is exposed and is brought from the protected region to the contact point on the sealing ring.

The covering layer may cover the outer conductor track completely or only partially on the exhaust gas side since, primarily, a complete interruption should be prevented.

The probe block forming the base body which is as a rule finger-shaped. The measuring sensor according to the invention may be composed of the ion-conducting solid electrolyte which is standard for producing measuring sensors of this type. Typically, the base body is composed, for example, of stabilised zirconium dioxide, for example of $ZrO_2$ stabilised with yttrium oxide or calcium oxide. Apart from stabilised $ZrO_2$, the base body may, however, also be made of solid electrolytes based on $CeO_2$, $HfO_2$ or $ThO_2$, which may be stabilised, for example, with CaO, MgO, SrO, $YbO_3$ and/or $Sc_2O_3$.

According to an advantageous development of the invention, the covering layer is composed of a densely sintered covering layer made of the raw material mixture of the base body ceramic having the same or enhanced sintering activity.

If, for example, the base body is composed of $ZrO_2$ stabilised with 5 mol-% yttrium oxide, a $ZrO_2$ material stabilised in this way can also be used to produce the covering layer.

The percentage composition of the raw material mixture used to form the covering layer does not, however, need to correspond to the composition of the probe block. Advantageously, however, the same or similar raw materials are used, but the percentage composition may also differ from one another. This means that the stabiliser content of the raw material mixture used to form a covering layer may differ from the stabiliser content of the raw material mixture of the probe block, for example, by up to 20%.

To produce the covering layer, a raw material mixture having enhanced sintering activity can, for example, also be used. An enhanced sintering activity is achieved, for example, by a more intense grinding and/or by adding a silicate flux, for example by adding Al silicate, Ba silicate or Ba Al silicate. Such additives may be added to the raw material mixture, for example, in amounts of about 5% by weight, referred to the raw material mixture.

Advantageously, spraying suspensions or printing pastes such as those described in greater detail in German Patent Specification 37 35 298 and corresponding U.S. Ser. No. 07/372,363, field Mar. 19, 1990, now abandoned, whose C-I-P is U.S. Ser. No. 07/807/163, filed Dec. 13, 1991 can be used to produce the covering layers.

Preferably, the layer thickness of the covering layers produced is 5 to 50 μm. It has as a rule been found particularly advantageous to largely match the layer thickness of the covering layer to the conductor track thickness, but not to allow the covering layer to become thinner than the conductor track in doing so.

The conductor track and the contact areas are composed of an electron-conducting material normally used to produce conductor tracks and contact areas, for example platinum, a platinum alloy, for example a platinum-rhodium alloy or a noble metal cermet, for example a platinum cermet.

Particularly advantageously, the conductor track and contact areas may have a supporting structure forming a matrix which can be sintered and which makes a largely porefree structure possible. Substances suitable for forming supporting structures with such sintering capability are, for example, stabilised zirconium dioxide powder. Typically, the conductor track may consequently consist, for example, of up to about 60–80% by volume of a Pt/Rh alloy and about 40–20% by volume of a stabilised $ZrO_2$ powder.

A complete integration of the conductor track in the base body just below the base body surface while using the covering layer according to the invention is possible when a Pt cermet conductor track with a supporting structure having sintering capability is used. Optionally, before the application of the covering layer to the conductor track, an additional insulating layer, for example of porously sintering $Al_2O_3$, which ensures the electrical insulation of the conductor track from the housing of the base body even at elevated temperatures (>500° C.), can also be applied to the conductor track beforehand.

The porous ceramic protective layer is of standard, known type.

DRAWING

FIGS. 1 and 2 show two exemplary embodiments of the invention, in side view, partially longitudinally sectioned. The measuring sensors shown, for example, in FIGS. 1 and 2 have the form of tubes which are closed at one end and of which the external surfaces are exposed to the gas to be measured and the internal surfaces to a reference gas. The measuring sensors are intended for installation in the exhaust gas pipe of an internal combustion engine of a motor vehicle for determining the λ-value and they are so constructed that they can be screwed into a threaded bore provided for the purpose and connected to an electronic control via a connecting cable.

DETAILED DESCRIPTION OF THE EXEMPLARY EMBODIMENTS

Figure 1:
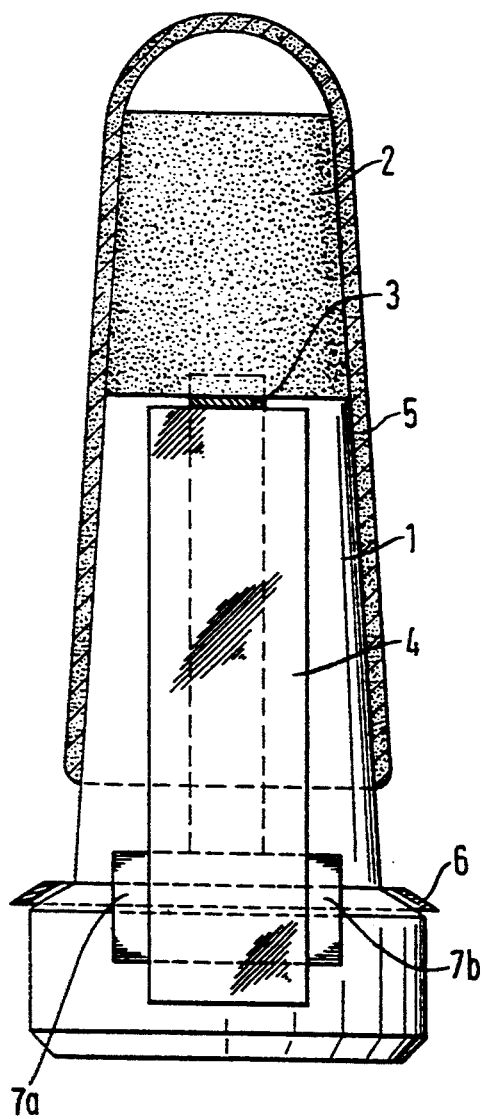
Figure 2:
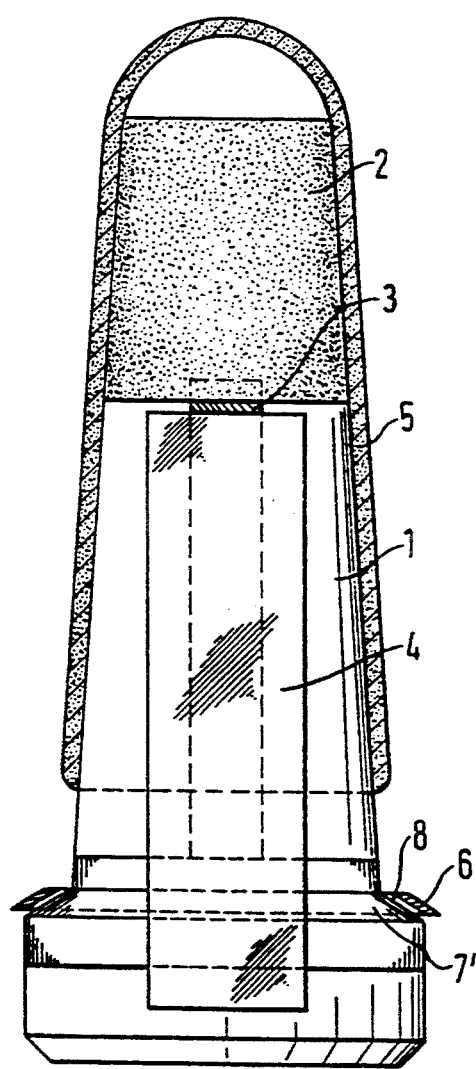

The electrochemical measuring sensors shown in FIGS. 1 and 2 are composed in both cases of a base body 1 made of an ion-conducting solid electrolyte of the type described in the form of a tube closed at one end, an inner electrode which is not shown and an outer electrode 2 disposed on the external surface of the probe block 1 as shown, that is, in the vicinity of the closed end. An elongated conductor track 3 having a connection side is covered by a covering layer 4. A ceramic protective layer 5 and a metallic sealing ring 6 are shown. The contacting areas are shown at 7.

The essential difference between the two electrochemical measuring sensors shown is that, in the case of the measuring sensor shown in FIG. 1, two contact areas 7a, 7b projecting from the region of the covering layer 4 are provided and these make contact with the metallic sealing ring 6, whereas, in the case of the measuring sensor shown in FIG. 2, a contact area 7' extends beneath ring 6 all around in a sealing groove 8 of the base body 1.

The embodiment shown in FIG. 1 is particularly efficient since the noble metal consumption, for example platinum consumption, for producing the contact areas is limited. The embodiment shown in FIG. 2 is, on the other hand, notable for making a particularly reliable contact, which in turn ensures a particularly favorable service life of the measuring sensor.

We claim:

1. Electrochemical measuring sensor for determining the oxygen content in exhaust gas from an internal combustion engine, having
   a base body (1) made of an ion-conductive solid electrolyte in the form of a tube having a closed end and an open end, adapted for mounting with said closed end of said tube projecting into an exhaust gas stream,
   an electrically conductive metallic sealing ring (6) circumferentially surrounding said tubular base body, intermediate said closed end and said open end, and for sealing said tube in an external structure,
   an outer electrode (2) located on the external surface of the tubular base body (1), in the region of the closed end thereof,
   a conductive track (3) extending along said external surface,
   a densely sintered covering layer (4) applied over at least most of said conductive track and protecting at least most of said conductive track (3) from attack by said exhaust gas,
   a porous ceramic protective layer (5) covering said outer electrode (2) completely and said conductive track (3) at least partially,
   wherein, in order to to minimize corrosive attack on said conductive track (3) by deposit of harmful gas constituents,
   the conductive track (3) and the covering layer (4) covering the conductive track (3) extend longitudinally along said base body, to a longitudinal position beneath said ring (6); and the conductive track (3) includes two contact surfaces (7a, 7b; 7') located beneath said metallic ring which project laterally from both sides of said conductive track (3) beyond said covering layer (4) and make electrical contact with said electrically conductive metallic sealing ring (6) at both sides of said conductive track (3).

2. Measuring sensor according to claim 1, wherein said base body (1) is formed, adjacent said sealing ring (6), with a sealing groove (8) and said contact surfaces comprise a contact ring (7') extending from both sides of the track (3) circumferentially around said body in said groove.

3. Measuring sensor according to claim 1, wherein the covering layer (4) is composed of a densely sintered covering layer made of the raw material mixture of the base body ceramic having the same or enhanced sintering activity.

4. Measuring sensor according to claim 1, wherein the covering layer (4) is composed of stabilised $ZrO_2$, optionally with flux addition.

5. Measuring sensor according to claim 1, wherein the covering layer (4) has a thickness which at least equals the thickness of the conductive track (3).

6. Measuring sensor according to claim 5, wherein the covering layer (4) has a layer thickness in the range between 5 micrometers and 50 micrometers.

7. Measuring sensor according to claim 1, wherein the conductive track (3) is a cermet conductor track and has a supporting structure or matrix of stabilized zirconium dioxide which has a sintering activity at least equal to that of said base body (1).

* * * * *